United States Patent
Kasuga et al.

(10) Patent No.: US 6,659,978 B1
(45) Date of Patent: Dec. 9, 2003

(54) PORTABLE DOSING APPARATUS

(75) Inventors: Masao Kasuga, Chiba (JP); Takayuki Kosaka, Chiba (JP); Akihiro Iino, Chiba (JP); Takashi Yamanaka, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 09/675,229

(22) Filed: Sep. 29, 2000

(30) Foreign Application Priority Data

Oct. 4, 1999 (JP) .......................................... 11-283448
Oct. 15, 1999 (JP) .......................................... 11-294228

(51) Int. Cl.[7] .............................................. A61M 1/00
(52) U.S. Cl. ........................ 604/151; 604/67; 604/890.1
(58) Field of Search ............................ 604/65–67, 132, 604/151, 248, 890.1

(56) References Cited

U.S. PATENT DOCUMENTS 4,976,687 A * 12/1990 Martin ......................... 604/65
5,582,593 A * 12/1996 Hultman ....................... 604/65
6,102,678 A * 8/2000 Peclat ....................... 417/477.7

* cited by examiner

Primary Examiner—Gregory L. Huson
Assistant Examiner—Peter deVore
(74) Attorney, Agent, or Firm—Adams & Wilks

(57) ABSTRACT

A low cost portable dosing apparatus enables the dispensing rate to be changed while enabling solution to be continuously dispensed to the body. The solution to be dispensed into the body is stored in a tank unit. A pump unit pumps the solution from the tank unit into the body of the patient. A controller controls pump unit operation. The tank unit, pump unit, and controller are attached to a wrist strap so that they can be easily connected and disconnected from each other. A compact, thin ultrasonic motor with high output per unit size drives the pump unit. A smaller pump unit is thus available, improving the portability of the apparatus. The ultrasonic motor is also substantially free of misoperation resulting from exposure to magnetic fields because the ultrasonic motor is not magnetically driven. Reliability is therefore improved.

29 Claims, 14 Drawing Sheets

FIGS. 11
FIG. 11A
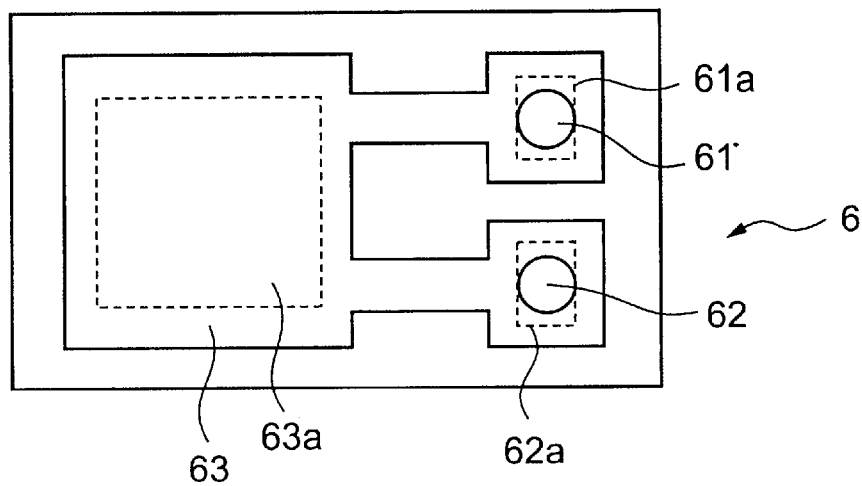
FIG. 11B
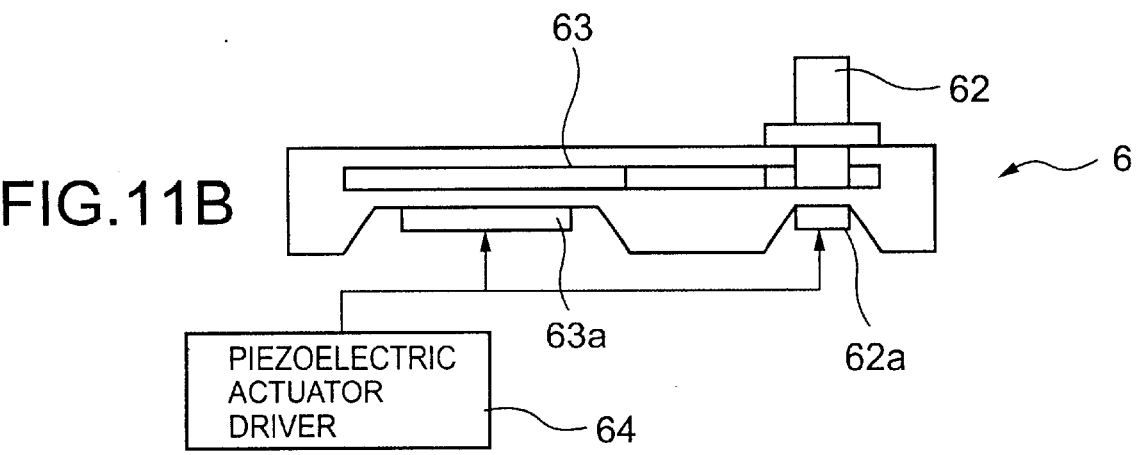

PORTABLE DOSING APPARATUS

BACKGROUND OF THE INVENTION

1. Field of the Invention

The present invention relates to a portable dosing apparatus that is capable of continuously dispensing a solution and varying the dispensing rate.

2. Description of Related Art

Portable drug dispensers that are worn by the patient and for dosing the patient with a drug are needed so that the patient can go about his or her normal daily activities while keeping his symptoms under control. Portable drug dispensers of this type include, for example, the compact peristaltic pump taught in Japanese Patent Publication Laid-Open No. 280763/1990, and the infusion pump taught in Japanese Patent Publication Laid-Open No. 236558/1987.

The peristaltic pump taught in Japanese Patent Publication Laid-Open No. 280763/1990 has a first module that is a pump module containing the injectable solution, and a second module that is a motor module containing both a controller and motor. Both the first and second modules can be installed and removed.

The infusion pump taught in Japanese Patent Publication Laid-Open No. 236558/1987 is an integrated unit, but the speed of the motor that is the source of pump drive power can be set manually, and the dispensing rate is therefore adjustable.

Problem to be Solved

The operating cost of this type of portable dosing apparatus should be low because it is used daily by the patient. It is also necessary to be able to adjust the dosing rate according to the patient's symptoms.

The dosing rate of the above-noted peristaltic pump, however, is determined by the motor module, and the motor module must therefore be replaced to change the dispensing rate. However, because the motor module is part of the solution delivery path, replacing the motor module to adjust the dispensing rate means that dosing stops temporarily. Plural motor modules must therefore be provided if the dispensing rate is to be adjustable, and the cost therefore rises.

While the dispensing rate is adjustable with the above-noted infusion pump, integration of all components into a single unit means that the entire unit must be replaced when the solution runs out. Dosing is therefore interrupted for a relatively long period of time, and operating cost is high.

Both of the prior art devices described above are also powered by a motor using magnetic flux as the drive power source, thus making the power unit larger and reducing device portability. What's more, the magnetic field generated by magnetic resonance imaging (MRI) and other magnetic medical devices could cause the power unit to be misoperated.

An object of the present invention is therefore to provide a low cost portable dosing apparatus with an adjustable dispensing rate that is capable of continuous dispensing even while changing the dispensing rate.

A further object of the present invention is to provide a portable dosing apparatus that uses a motor that does not use magnetic flux, as the drive power source, and thereby achieves greater compactness and increased reliability.

SUMMARY OF THE INVENTION

To achieve the above objects, a portable dosing apparatus (1) for continuously dosing a body with a solution at a dispensing rate that can be varied comprises, according to the present invention, a tank unit (2) for holding the solution, a pump unit (3) for pumping the solution from the tank unit to the body, and a controller (4) for controlling the pump unit, configured such that the tank unit, pump unit, and controller each being freely connectable and disconnectable.

Thus comprised, the dispensing rate can be changed simply by changing the controller. In other words, because it is not necessary to replace any part of the solution dispensing path in order to change the dispensing rate, the time during which dispensing is interrupted when changing the dispensing rate is extremely short.

Furthermore, it is only necessary to replace the tank unit when the solution runs out. In addition, the relatively high cost but same pump unit is used for a specific period of time. Operating cost is therefore low.

It will also be noted that the portable dosing apparatus of our invention is not limited to use with humans, but can also be used with animals.

Furthermore, by further providing a means for securing the portable dosing apparatus to the body, such as wrist strap 11, the portable dosing apparatus can be easily attached to the body. Such an exemplary means is a strap like that of a wristwatch.

The controller typically comprises a CPU, a reference signal generating circuit for CPU operation, and a ROM for storing a control program. The controller in our invention, however, additionally has a dispensing parameter input means (such as buttons 41b) for externally inputting dispensing parameters, and a display (44) for displaying dispensing parameters so that the controller can control the pump unit according to the dispensing parameters.

It is yet further possible to adjust the dosage, dispensing rate, and other dispensing conditions while confirming the information on a display. It is therefore possible to easily and reliably change the dispensing parameters without replacing the controller.

Yet further preferably, the portable dosing apparatus also has a status information input means (42) for inputting status information indicative of a condition of the body. In this case the controller controls the pump unit according to status information from this status information input means.

If such patient information as the heart rate, blood pressure, blood sugar, is entered, the controller can, using the control program stored to ROM, for example, use the supplied information to control the pump unit. As a result, dosage can be easily optimally adjusted even if a person with specialist knowledge is not present.

The tank unit of this portable dosing apparatus preferably has a solution tank (21) that is expandable for internally storing the solution; and a pressure applying means (23) for applying pressure to the solution tank in a direction reducing an internal volume of the solution tank so as to pressurize the solution.

The pressure applying means (23) can thus pressurize the solution in the solution tank, enabling the solution to flow easily from the solution tank. The load on the pump unit upon dispensing is therefore low, and solution's backflow is suppressed.

The pump unit preferably has an actuator driven according to a drive signal from the controller; a drive power transfer mechanism (such as gear train 34) for transferring drive power from the actuator; and a pump (33) for pumping solution by means of drive power transferred from the drive power transfer mechanism.

This actuator is preferably an ultrasonic motor (5) or a piezoelectric actuator.

By using a compact ultrasonic motor or piezoelectric actuator with high output per unit volume as the drive source for the pump unit, the size of the pump unit is reduced and the portability of the portable dosing apparatus is improved.

Furthermore, because the ultrasonic motor and piezoelectric actuator are not magnetically driven, there is substantially no chance of misoperation when close to a magnetic device. The reliability of the portable dosing apparatus is thus improved.

Further, the pump unit preferably comprises an actuator driven according to a drive signal from the controller; and a pump (73) for pumping solution rotatively by means of drive power transferred directly from the actuator.

This actuator in this case is again preferably an ultrasonic motor (8) or a piezoelectric actuator (63a).

By using a compact ultrasonic motor or piezoelectric actuator with high output per unit volume as the drive source for the pump unit, the size of the pump unit is reduced and the portability of the portable dosing apparatus is improved.

Furthermore, because the ultrasonic motor and piezoelectric actuator are not magnetically driven, there is substantially no chance of misoperation when close to a magnetic device. The reliability of the portable dosing apparatus is thus improved.

Furthermore, because the ultrasonic motor or piezoelectric actuator directly drive the pump unit, a power transfer mechanism is not needed, and a compact, lightweight pump unit can thus be achieved.

Furthermore, the number of the parts is reduced, thus minimizing the manufacturing cost.

The portable dosing apparatus further preferably comprises an operation detection means (such as rotational distance detector 37) for detecting pump unit operation and outputting a detection signal to the controller.

The reliability of the portable dosing apparatus is yet further improved as a result of the controller controlling the pump unit while monitoring pump unit operation.

Yet further preferably, the portable dosing apparatus additionally has a backflow prevention means (such as ratchet 33e) preventing the pump unit from operating in reverse.

In this case the backflow prevention means significantly lowers the chances that the pump will operate in reverse or the solution backflow will occur. The reliability of the portable dosing apparatus is thus yet further improved.

Yet further preferably, the portable dosing apparatus also has a needle (12) for injecting solution to the body.

Other objects and attainments together with a fuller understanding of the invention will become apparent and appreciated by referring to the following description and claims taken in conjunction with the accompanying drawings.

BRIEF DESCRIPTION OF THE DRAWINGS

FIG. 11A is a top view of an alternative version of pump unit 3, and FIG. 11B is a section view of the same;

DESCRIPTION OF THE PREFERRED EMBODIMENTS

Embodiment 1

A first preferred embodiment of a portable dosing apparatus according to the present invention is described below with reference to the accompanying FIGS. 1 to 10.

Figure 1:
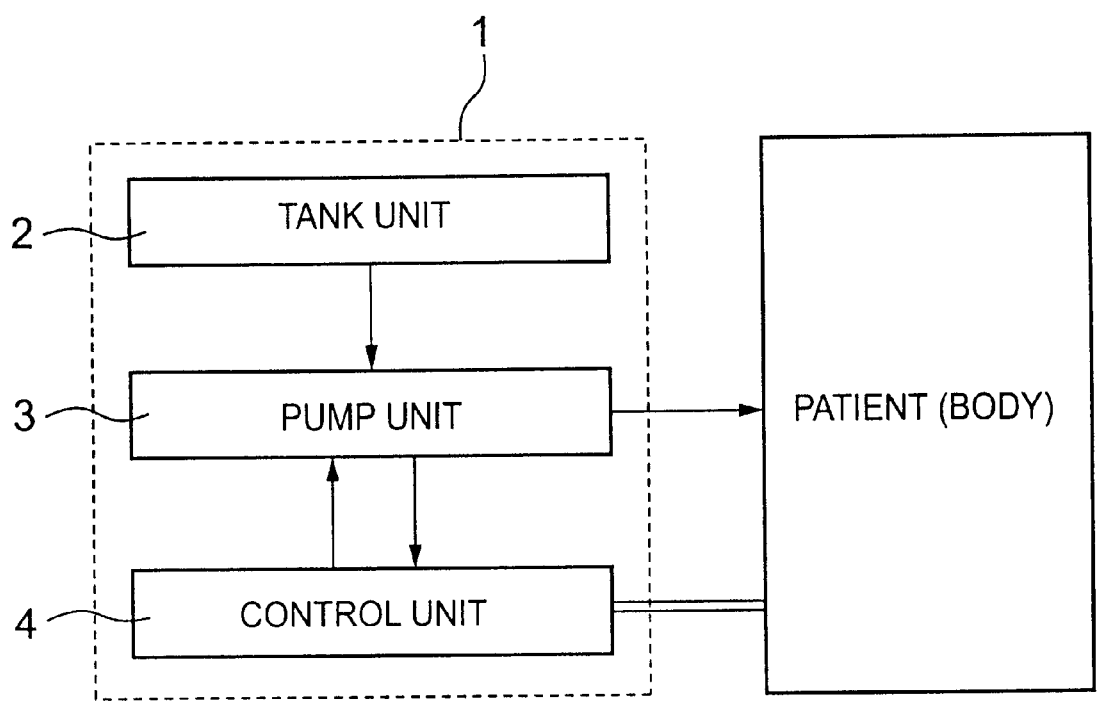
FIG. 1 is a block diagram of a portable dosing apparatus according to a first embodiment of the present invention.
Figure 2:
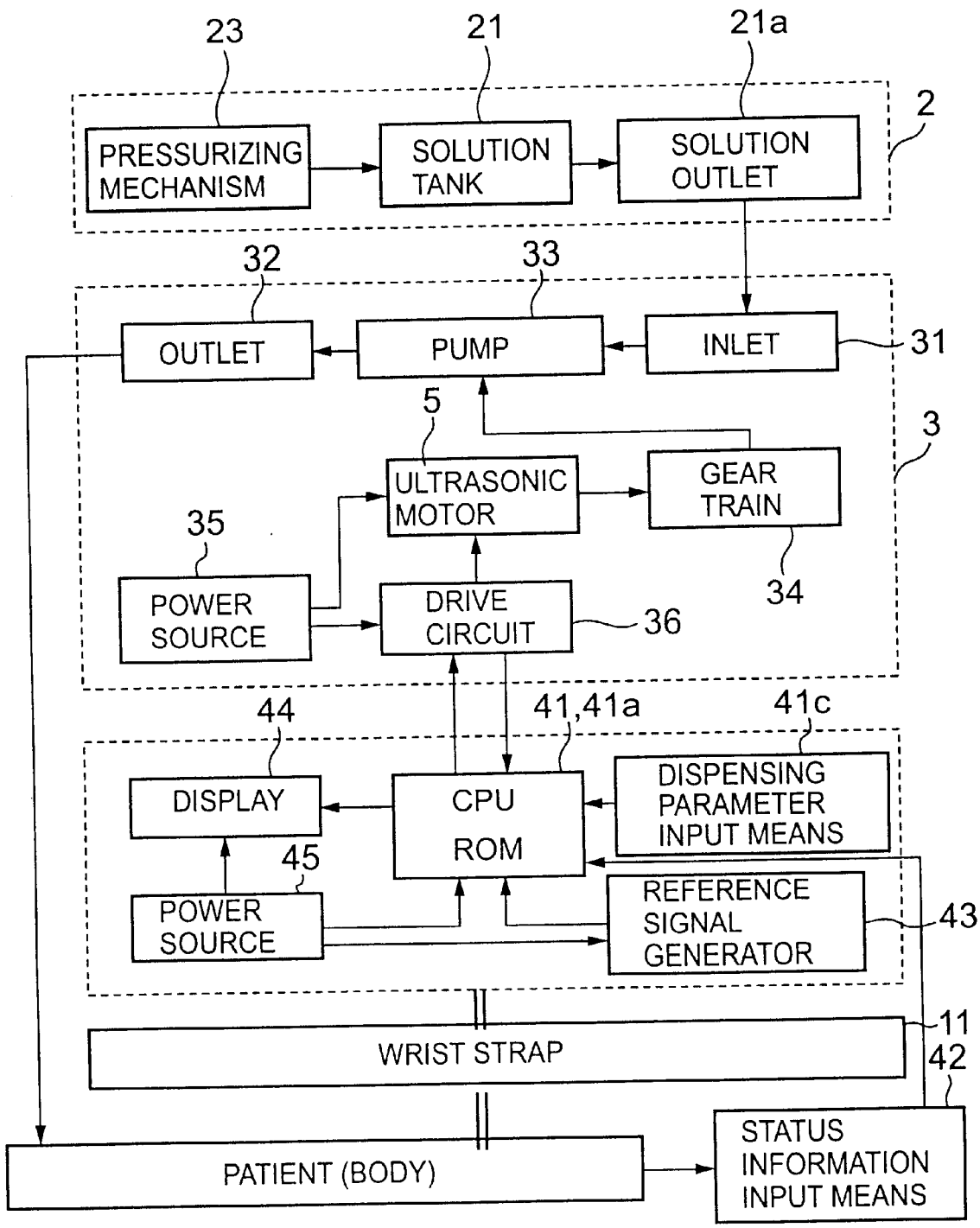
FIG. 2 is a more detailed block diagram of the portable dosing apparatus 1 shown in FIG. 1.

FIG. 1 is a block diagram of this portable dosing apparatus 1 comprising a tank unit 2, pump unit 3, and control unit 4. FIG. 2 is a more detailed block diagram of the components shown in FIG. 1.

Figure 3:
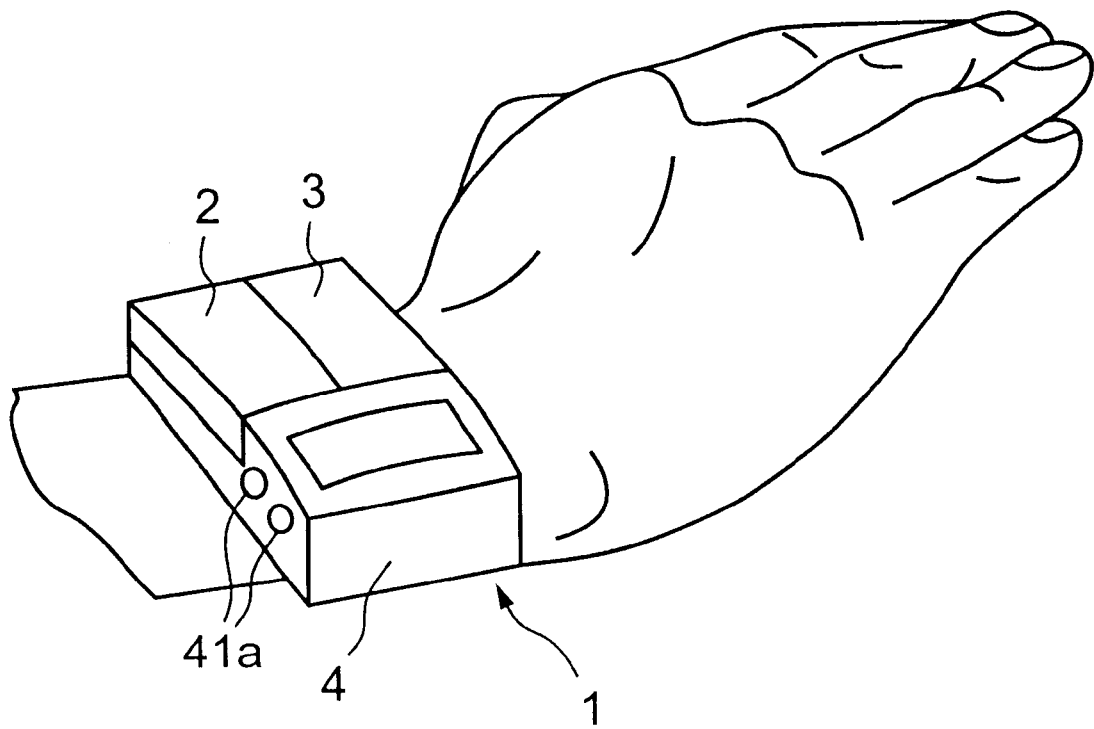
FIGS. 3 and 4 show how the portable dosing apparatus 1 is typically worn by a user.
Figure 4:
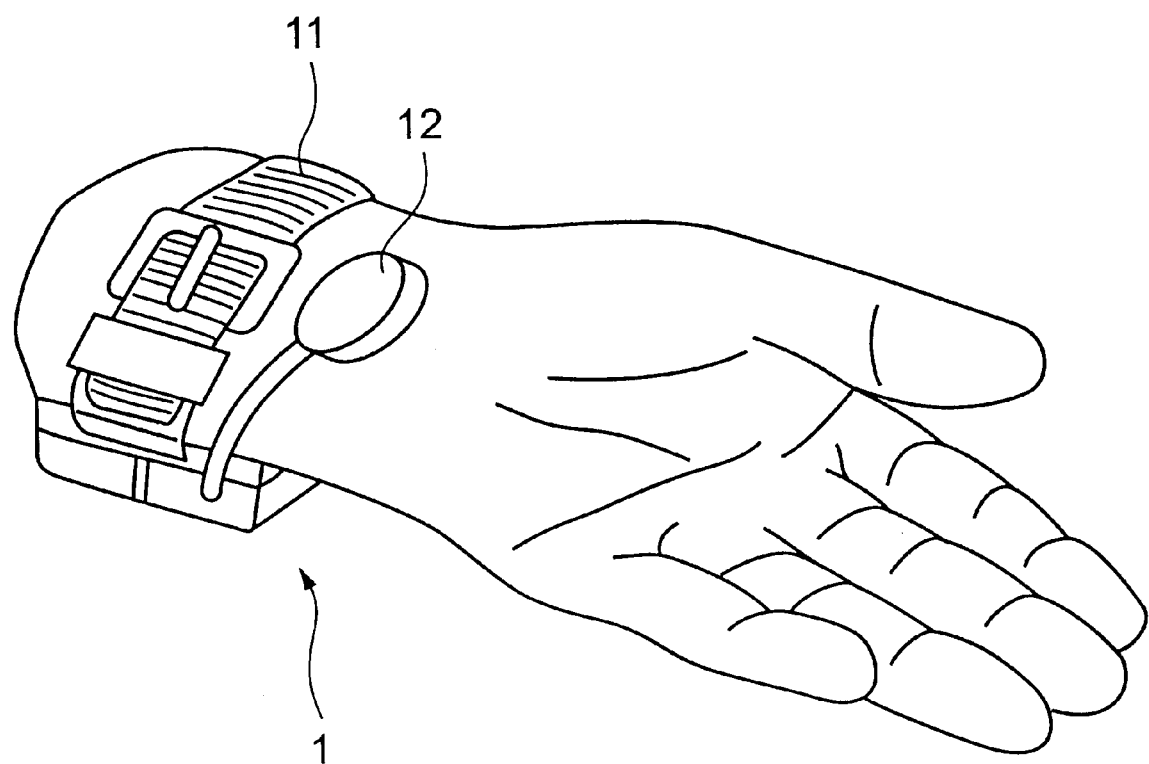

FIGS. 3 and 4 illustrate how the portable dosing apparatus 1 is typically worn by a user.

Figure 5:
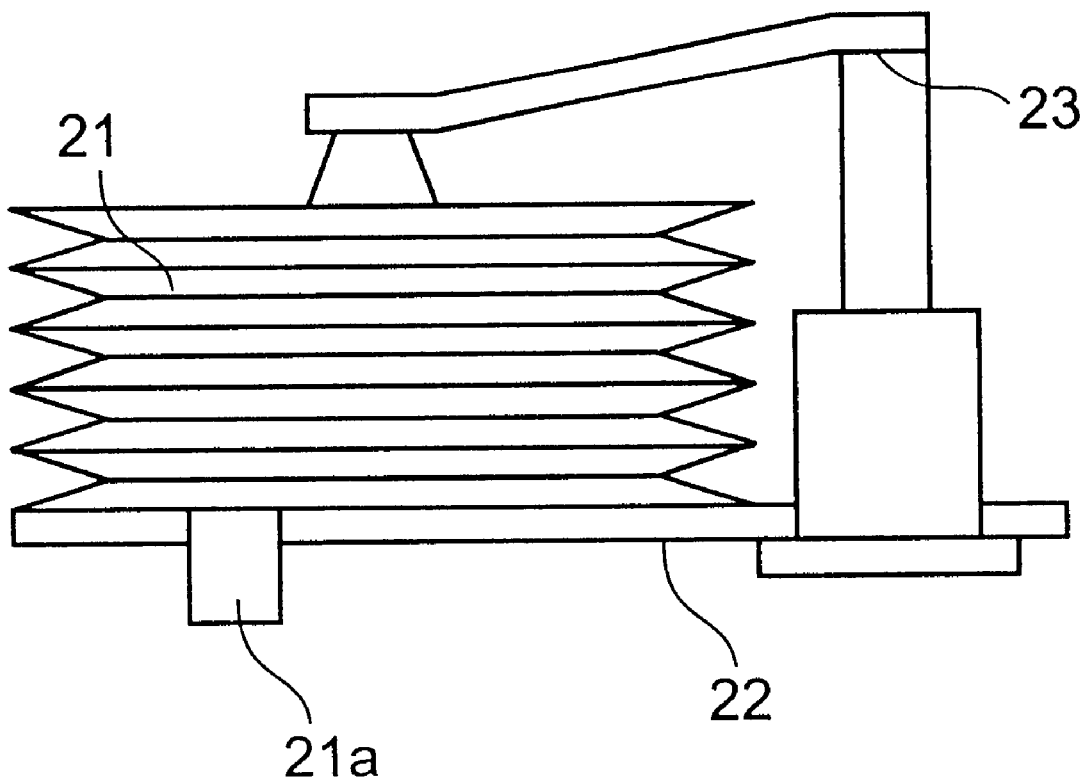
FIG. 5 is a side view of the tank unit 2 shown in FIG.
Figure 6:
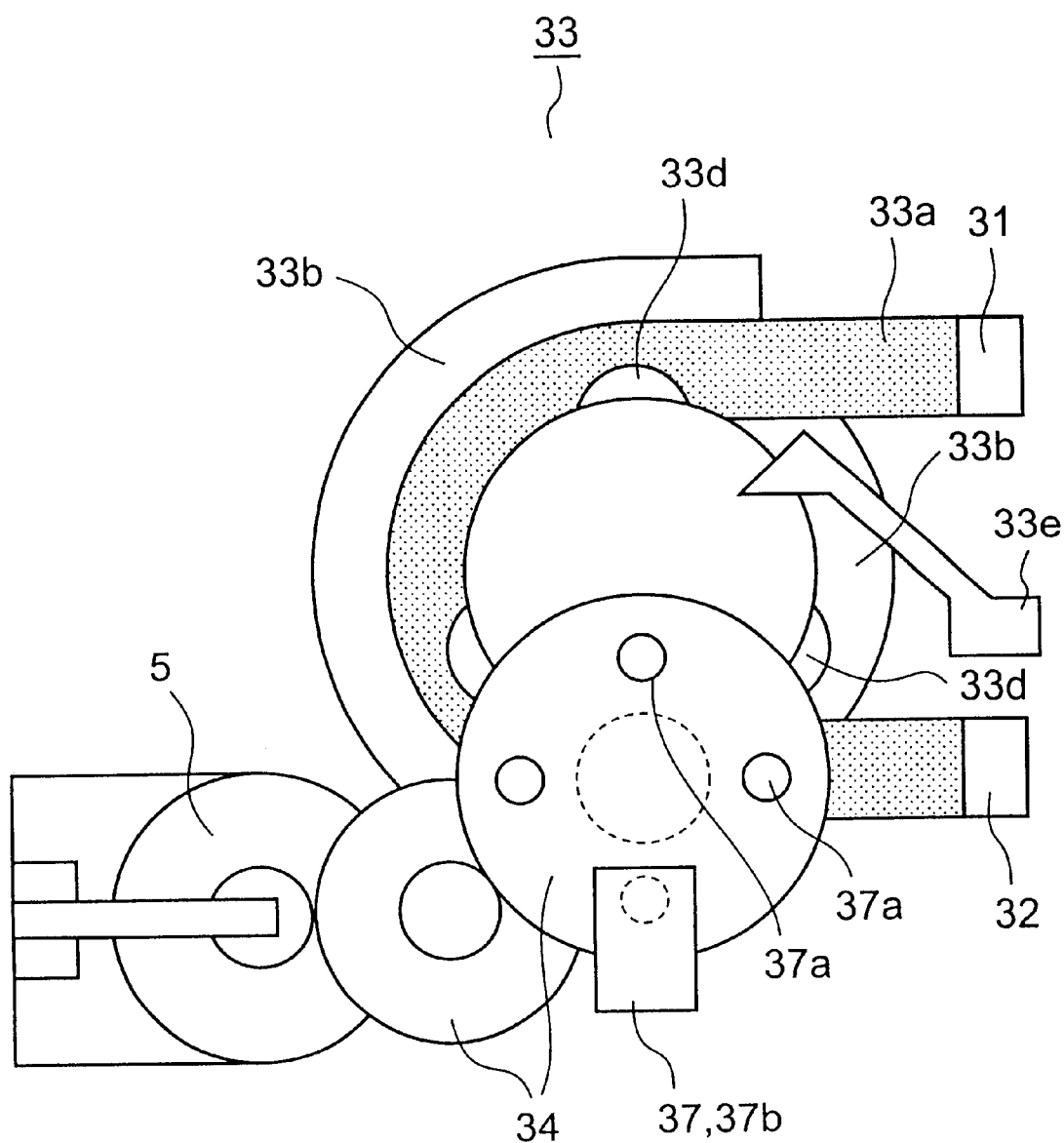
FIG. 6 is a top view of the pump unit 3 shown in FIG. 1.
Figure 7:
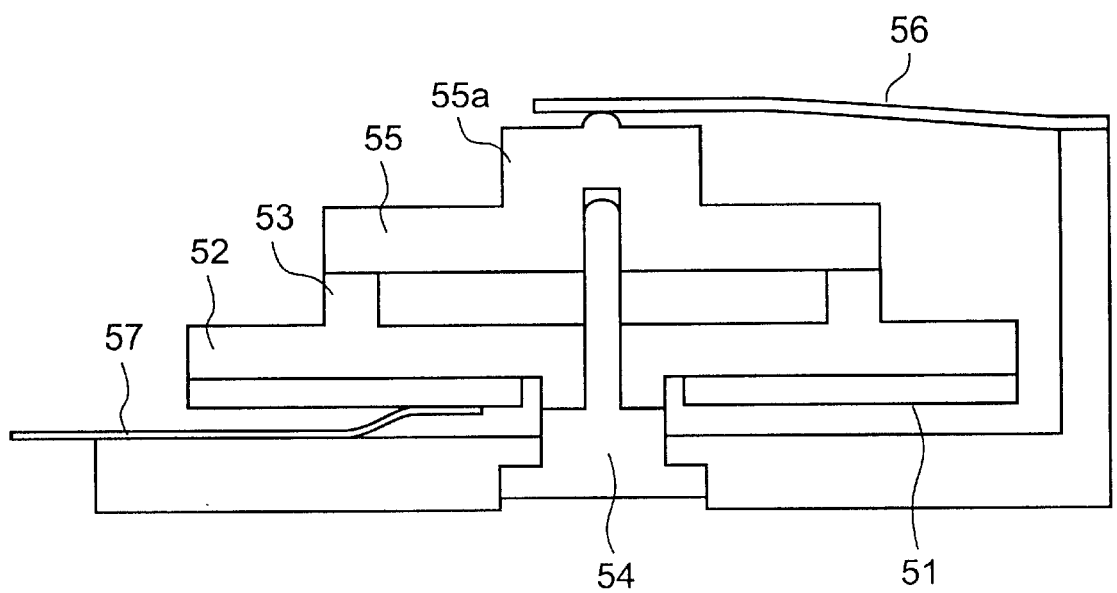
FIG. 7 is a section view of an ultrasonic motor 5 that is the power source for pump unit 3 in the first embodiment shown in FIG. 1.
Figure 8:
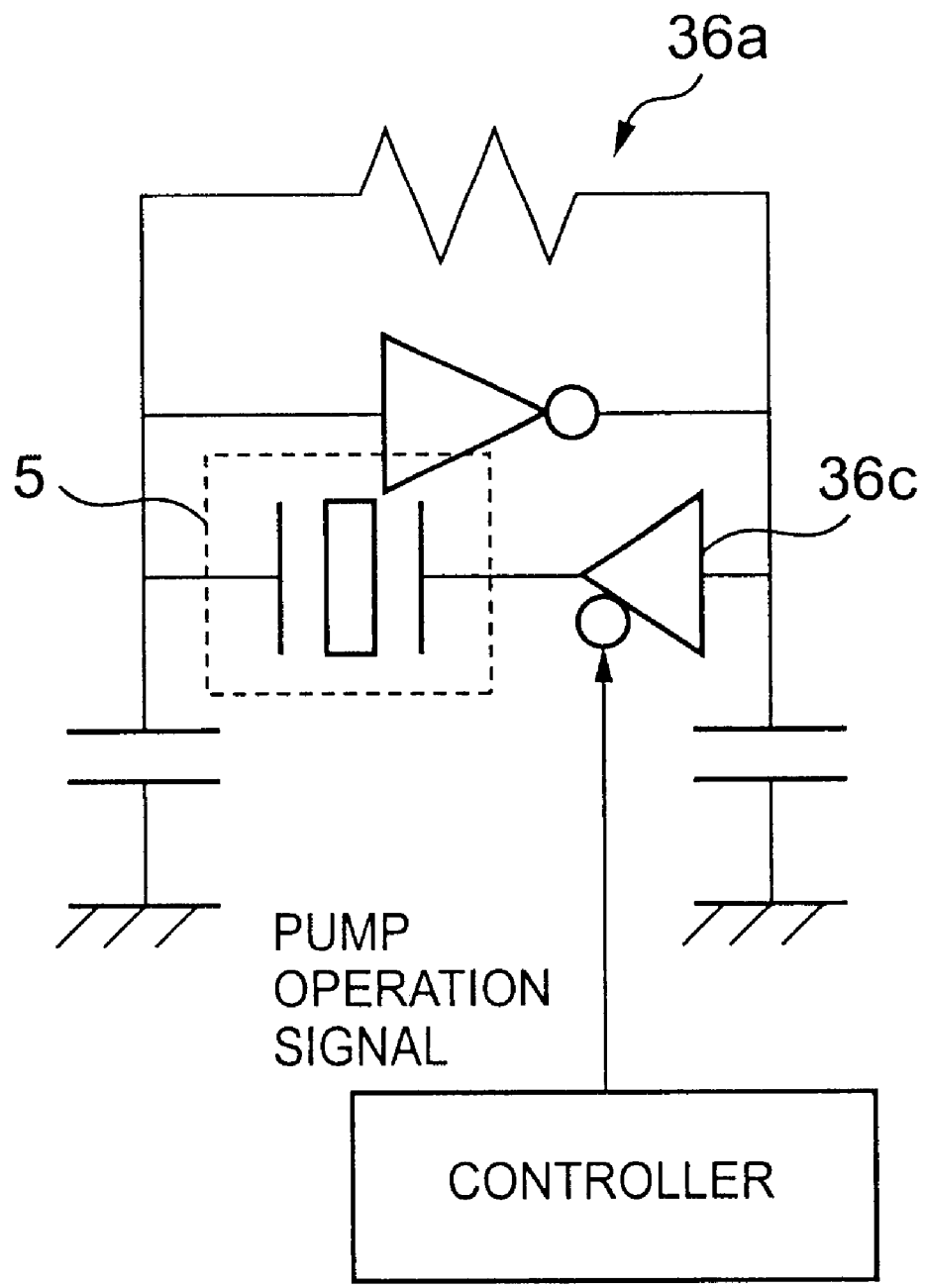
FIG. 8 is a circuit diagram of the drive signal generating circuit of ultrasonic motor 5 in the first embodiment shown in FIG. 1.
Figure 9:
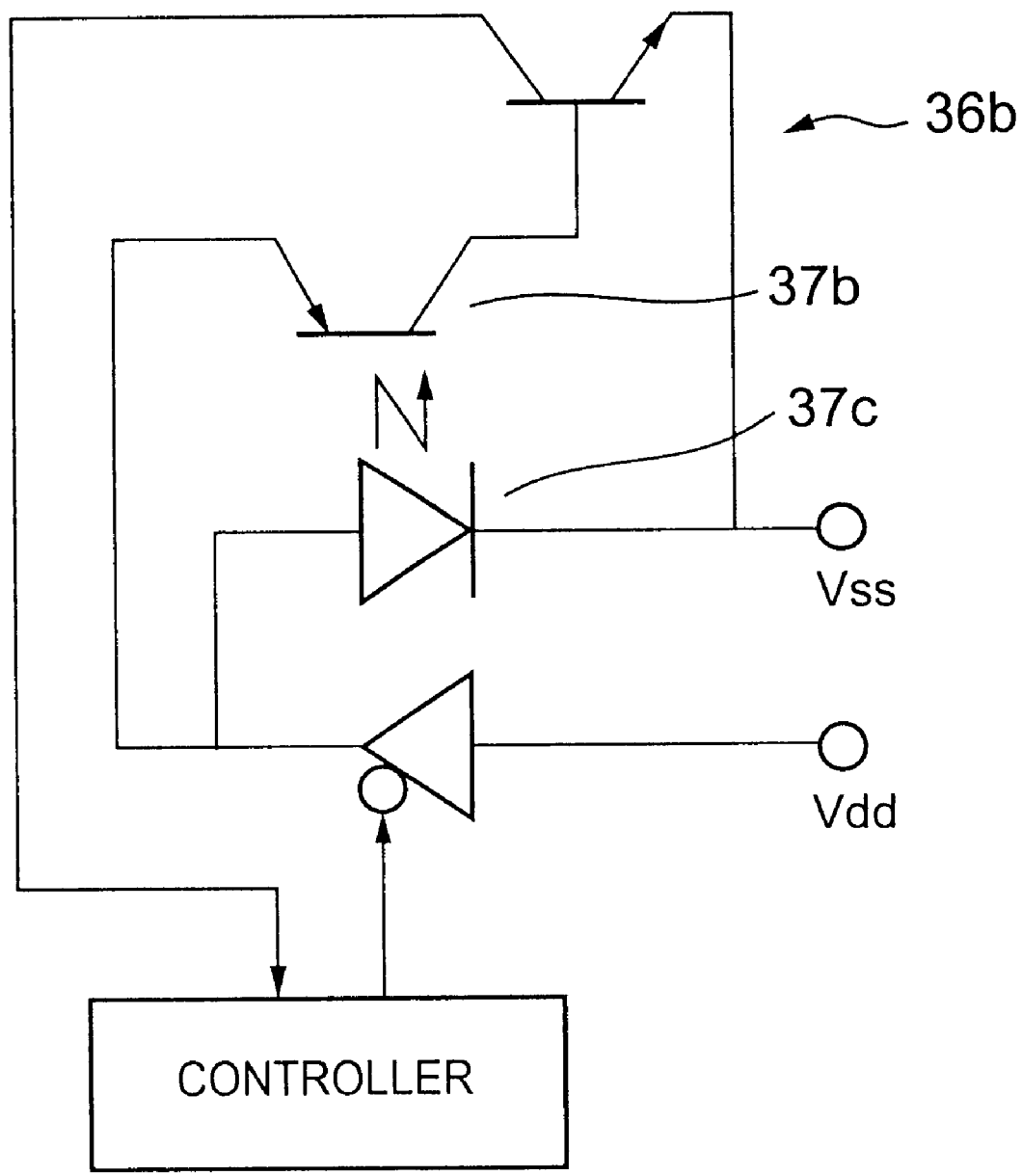
FIG. 9 is a circuit diagram of the drive state detection circuit for detecting operation of pump unit 3 in the first embodiment shown in FIG. 1.
Figure 10:
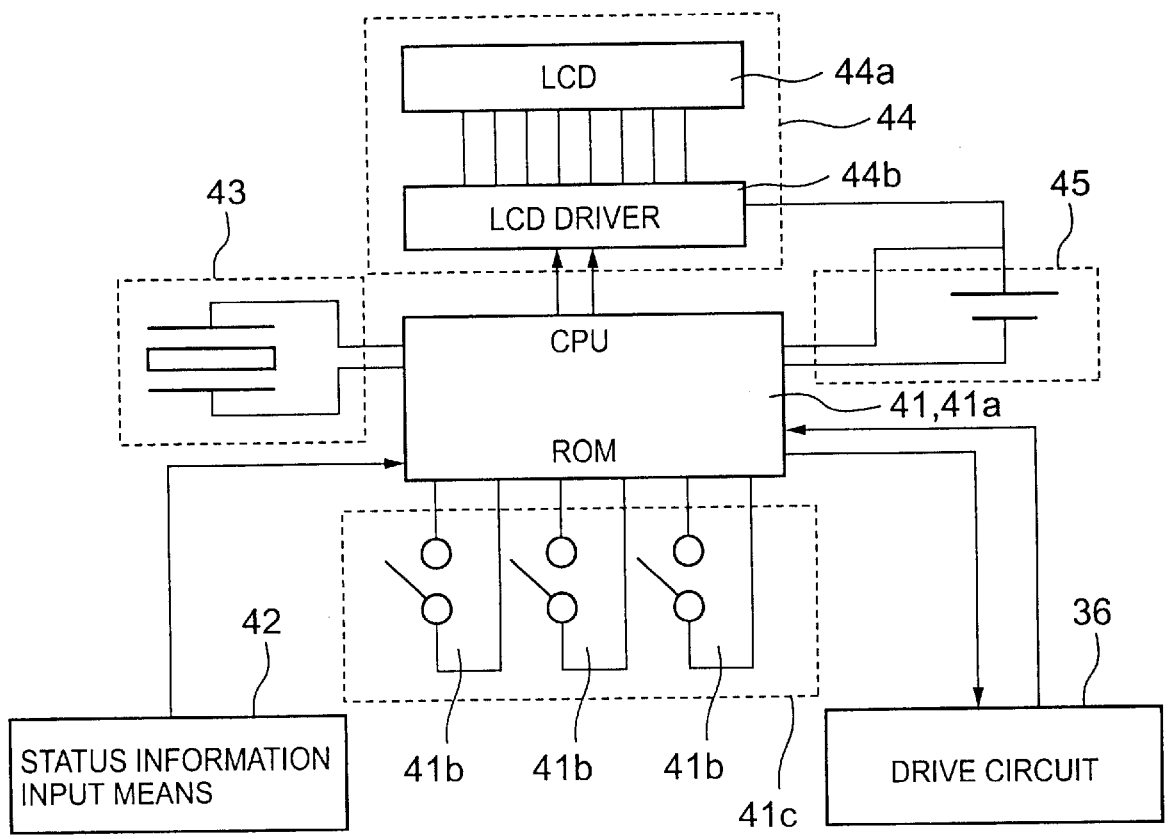
FIG. 10 is a block diagram of the control unit 4 in the first embodiment shown in FIG. 1.

FIG. 5 is a side view of the tank unit 2 shown in FIG. 1. FIG. 6 is a top view of the pump unit 3. FIG. 7 is a section view showing details of an ultrasonic motor 5 that is the power source for pump unit 3. FIG. 8 is a circuit diagram of the drive signal generating circuit 36a of ultrasonic motor 5, and FIG. 9 is a circuit diagram of the drive state detection circuit 36b for detecting operation of pump unit 3. FIG. 10 is a block diagram of the control unit 4.

Referring to FIG. 1, the tank unit 2 of the portable dosing apparatus 1 internally holds the solution to be dispensed; the pump unit 3 dispenses the solution from tank unit 2 to the patient; and the control unit 4 controls the pump unit 3. As shown in FIGS. 2, 3, and 4, these units are attached to a wrist strap 11 so that they can be connected and disconnected from each other.

As described more fully below, the control unit 4 controls pump unit 3 to adjust the dispensing rate according to such patient information as the blood pressure, heart rate, and blood sugar. The control unit 4 also monitors pump unit 3 drive status.

As shown in FIG. 4, solution pumped by pump unit 3 is injected into the patient's body by way of needle 12.

As shown in FIG. 2 and FIG. 5, tank unit 2 has a bellows-like solution tank 21 disposed on a base 22, and a pressurizing mechanism 23 whereby force can be applied so as to push down on solution tank 21.

Solution outlet 21a for connecting solution tank 21 to the inlet 31 of pump unit 3, further described below, is disposed on the bottom of solution tank 21 passing through base 22.

It should be noted that solution tank 21 shown in is FIG. 5 inflated by the solution stored therein. The solution in solution tank 21 is thus pressurized by the force applied from pressurizing mechanism 23 and the compressive force of the solution tank 21 itself.

As shown in FIG. 2 and FIG. 6, pump unit 3 has an inlet 31 through which solution is introduced to the pump unit 3, an outlet 32 from which solution leaves the pump unit 3, a pump 33 for pumping solution introduced from inlet 31 out from outlet 32, an ultrasonic motor 5 for driving pump 33 by means of intervening gear train 34, ultrasonic motor power source 35, and ultrasonic motor drive circuit 36.

As shown in FIG. 6, pump 33 has a flexible tube 33a connecting inlet 31 and outlet 32 disposed along the inside wall of a hollow circular container 33b. A disc 33c turned by drive power from ultrasonic motor 5 is disposed coaxially to and inside circular container 33b. Independently rotating rollers 33d are disposed at 120 degree intervals around the side of disc 33c so that the rollers 33d press against flexible tube 33a.

Pump 33 is thus a pump that pushes solution inside flexible tube 33a from inlet 31 to outlet 32 as a result of rollers 33d pushing against and rotating along the surface of flexible tube 33a.

To mechanically prevent disc 33c from rotating in the opposite direction, a ratchet 33e (backflow prevention means) is also disposed to disc 33c.

A rotational distance detector 37 (operation detection means) is further disposed to one of the gears of gear train 34. This rotational distance detector 37 has a plurality of holes 37a in the gear spaced at a constant angular increment, a light emitting means, and a photodiode 37b. This rotational distance detector 37 detects the distance of gear train 34, that is disc 33c, rotation, and outputs a detection signal to control unit 4 by way of drive circuit 36.

As shown in FIG. 7, ultrasonic motor 5 has a disc-shaped piezoelectric element 51; disc-shaped vibrator 52 fixed to the top of piezoelectric element 51; a plurality of protrusions 53 disposed integrally to the top of vibrator 52; a spindle 54 passing through the centers of piezoelectric element 51 and vibrator 52 and supporting them on a base; a rotor 55 supported and rotating freely on spindle 54; leaf spring 56 urging rotor 55 against protrusions 53; and lead 57 for transmitting a drive signal from drive circuit 36 to piezoelectric element 51.

It should be noted that rotor 55 has on top a gear 55a that meshes with gear train 34. In addition, piezoelectric element 51 is divided circumferentially into, for example, six parts, these parts being alternately polarized oppositely and divided each in two equal parts. The protrusions 53 are disposed at the border between these polarized segments such that one protrusion 53 is located at every other polarized segment.

This ultrasonic motor 5 converts electrical energy directly into mechanical energy, features high output per unit volume, and is resistant to effects from a magnetic field.

The drive circuit 36 comprises a drive signal generating circuit 36a as shown in FIG. 8, and a drive state detection circuit 36b as shown in FIG. 9.

The drive signal generating circuit 36a is a common self-oscillation circuit as generally used in ultrasonic motor drive circuits. Tri-state buffer 36c for drive signal output is controlled by control unit 4.

Drive state detection circuit 36b amplifies and outputs a signal detected by photodiode 37b based on a signal generated by light emitting means 37c, which may be an LED. Drive state detection circuit 36b is turned on and off by control unit 4.

As shown in FIG. 2 and FIG. 10, control unit 4 has a CPU 41 for directly controlling drive circuit 36; ROM 41a to which a control program is prestored; dispensing parameter input means 41c such as buttons 41b for inputting a user-generated signal to CPU 41; reference signal generator 43 for generating a reference signal for driving CPU 41; display 44 for displaying the dispensing rate, dose, and biological information as controlled by CPU 41; and power source 45.

A status information input means 42 can also be provided for inputting to CPU 41 a signal indicative of the patient condition.

As shown in FIG. 10, display 44 consists basically of an LCD panel 44a and LCD driver 44b. CPU 41 has a plurality of buttons 41b as the dispensing parameter input means, including an on/off button, dispensing rate adjusting button, and an interval adjustment button.

Following the control program stored to ROM 41a, CPU 41 controls ultrasonic motor 5 according to a signal input from buttons 41b and status information input means 42 to adjust the dosage (volume) and dispensing rate.

When the solution is consumed and must be replenished with the portable dosing apparatus 1 described above, it is only necessary to replace tank unit 2. Operating cost is therefore low.

Furthermore, the dosage and dispensing rate can be adjusted while confirming the dispensing conditions on display 44. It is also possible to replace only the control unit 4 to adjust the dispensing conditions. As a result, it is not necessary to remove or replace any part of the dispensing path in order to change the dispensing conditions. Dispensing the solution is interrupted for only a very short time when changing the dispensing rate.

The dosage can also be easily adjusted to be optimum even when a person with specialized knowledge is not present because control unit 4 can automatically adjust dispensing conditions according to patient information detected and supplied from status information input means 42.

Furthermore, the load on ultrasonic motor 5 is small because pressurizing mechanism 23 and solution tank 21 both pressurize the solution in solution tank 21, and the solution is thus able to flow easily from the solution tank 21.

Yet further, by using a compact ultrasonic motor 5 featuring high output per unit volume as the drive source for pump unit 3, the size of the pump unit is reduced and the portability of the portable dosing apparatus is thereby improved.

Yet further, because the ultrasonic motor 5 is not magnetically driven there is substantially no possibility of misoperation when close to a magnetic device, that is, when exposed to a magnetic field. The reliability of the portable dosing apparatus 1 is thereby further improved.

The control unit 4 can also control pump unit 3 while monitoring the pump unit 3 operating status by means of rotational distance detector 37 and drive state detection circuit 36b. Pump unit 3 is also prevented by the ratchet 33e from operating in reverse, thereby yet further improving the reliability of the portable dosing apparatus 1.

Embodiment 2

Figure 12:
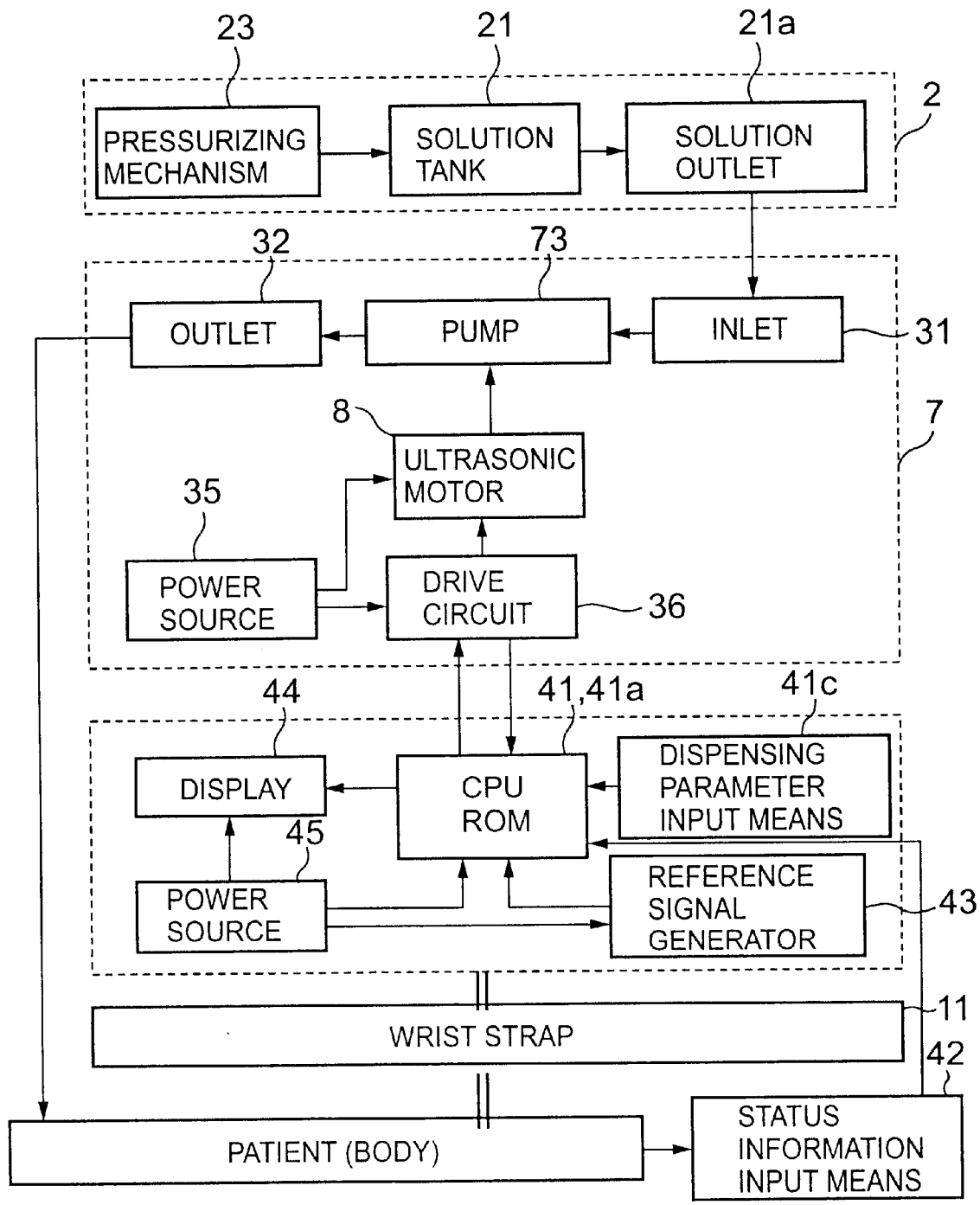
FIG. 12 is a block diagram of a portable dosing apparatus according to a second preferred embodiment of the invention.
Figure 13:
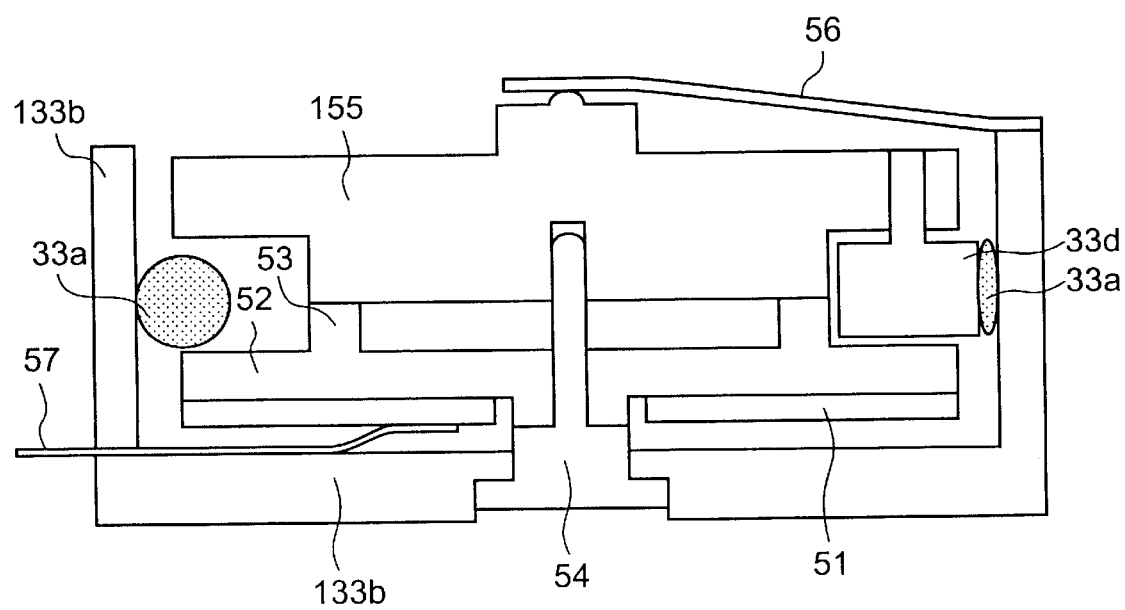
FIG. 13 is a section view of the pump 73 and ultrasonic motor 8 in the second preferred embodiment of the invention shown in FIG. 12.
Figure 14:
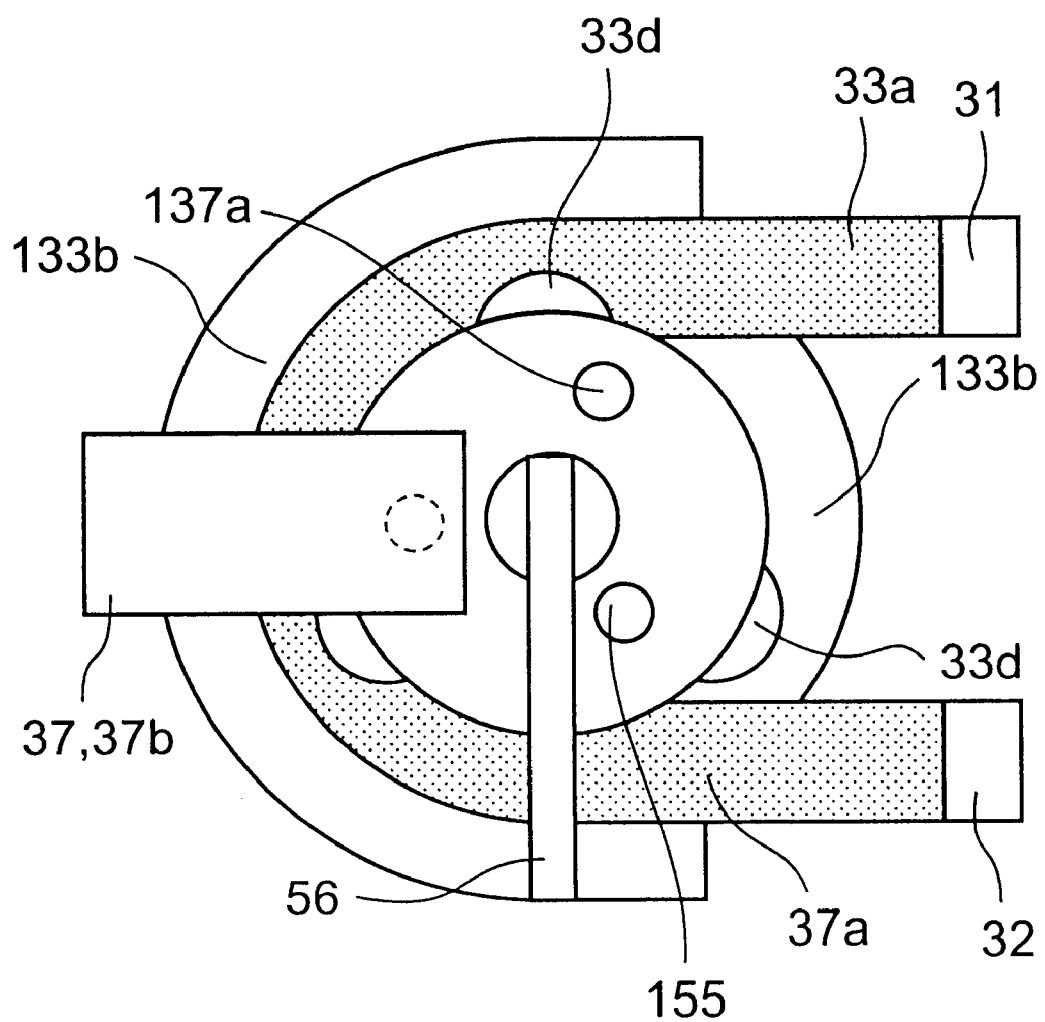
FIG. 14 is a plan view of the pump 73 and ultrasonic motor 8 in the second preferred embodiment of the invention shown in FIG. 12.

The portable dosing apparatus 2 according to this second embodiment of the invention uses the pump unit 7 shown in FIGS. 12 to 14 in place of the pump unit 3 of the first embodiment. FIG. 12 is a detailed block diagram of this portable dosing apparatus 122, FIG. 13 is a section view of the pump unit 7, and FIG. 14 is a plan view of the pump unit 7.

It should be noted that like parts in this second embodiment and the first embodiment described above are identified by like reference numeral, and further description thereof is thus omitted below.

Pump unit 3 and pump unit 7 differ in that whereas pump unit 3 comprises ultrasonic motor 5, outlet 32, inlet 31, gear train 34, drive circuit 36, power source 35, and pump 33, and pump 33 is driven by ultrasonic motor 5 by way of gear train 34, pump unit 7 does not have a gear train 34. The ultrasonic motor 8 used in pump unit 7 in place of ultrasonic motor 5 directly drives pump 73, which replaces pump 33.

This is described in further detail below.

As shown in FIG. 12, FIG. 13, and FIG. 14, pump unit 7 comprises inlet 31 and outlet 32, pump 73 for pumping solution in from inlet 31 and out from outlet 32, ultrasonic motor 8 for directly driving pump 73, power source 35 for ultrasonic motor 8, and ultrasonic motor drive circuit 36.

As shown in FIG. 14, pump 73 has a flexible tube 33a connecting inlet 31 and outlet 32 disposed along the inside wall of a hollow circular container 133b. ultrasonic motor 8 is disposed in circular container 133b so that the motor rotor 155 is concentric to circular container 133b. Independently rotating rollers 33d are disposed at 120 degree intervals around the side of rotor 155 so that the rollers 33d press against flexible tube 33a. It should be noted that rotor 155 and ultrasonic motor 8 are not contained in pump 73, and are further described below.

Pump 73 is thus a pump that pushes solution inside flexible tube 33a from inlet 31 to outlet 32 as a result of rollers 33d pushing against and rotating along the surface of flexible tube 33a.

A plurality of reflectors 137a are disposed at a constant angular interval around rotor 155 on the side thereof opposite the surface that contacts protrusions 53. The rotational distance detector 37 (operation detection means) comprising a light emitting means and photodiode 37b is disposed above reflectors 137a with a specific gap therebetween. The rotational distance detector 37 thus detects the distance of rotor 155 rotation, and supplies a corresponding detection signal to control unit 4 by way of drive circuit 36.

As shown in FIG. 13, the ultrasonic motor 8 has a disc-shaped piezoelectric element 51; disc-shaped vibrator 52 fixed to the top of piezoelectric element 51; a plurality of protrusions 53 disposed integrally to the top of vibrator 52; a spindle 54 passing through the centers of piezoelectric element 51 and vibrator 52 and supporting them on a base; rotor 155 supported and rotating freely on spindle 54; leaf spring 56 urging rotor 155 against protrusions 53; and lead 57 for transmitting a drive signal from drive circuit 36 to piezoelectric element 51. It will be remembered that rollers 33d are disposed to rotor 155 in this exemplary embodiment.

By thus disposing rollers 33d to rotor 155 and placing the flexible tube 33a around the outside of rotor 155 so that it is squeezed between rollers 33d and circular container 133b, pump 73 can be driven directly by ultrasonic motor 8. By thus eliminating gear train 34, pump unit 7 can be effectively downsized. Assembly is also simplified, and manufacturing cost is reduced, because the number of parts is also reduced.

It will also be obvious to one with ordinary skill in the related art that the present invention shall not be limited to the above described preferred embodiments and can be varied in many ways without departing from the scope of the accompanying claims.

For example, a pump unit 6 shown in FIG. 11 can be used in place of pump unit 3.

As shown in the plan view in FIG. 11A and the section view in FIG. 11B, pump unit 6 has inlet 61, outlet 62 and a storage compartment 63. Inlet 61 and outlet 62 open and close by means of a piezoelectric actuator 61a, 62a, respectively. A storage compartment 63 connected to inlet 61 and outlet 62 temporarily stores solution. This pump unit 6 is driven by a piezoelectric actuator driver 64.

A piezoelectric actuator 63a is also disposed to one side of storage compartment 63. Piezoelectric actuator 63a can be driven to expand or contract itself, thus to change and adjust the capacity of storage compartment 63.

In other words, pump unit 6 operates by opening only inlet 61, expanding storage compartment 63 to draw solution therein, then closing inlet 61 and opening outlet 62, and then compressing (contracting) storage compartment 63 to propel solution from outlet 62. The benefits described above can also be achieved with this pump unit 6.

It should be noted that other than making the portable dosing apparatus larger and more susceptible to the effects of magnetic fields, a portable dosing apparatus according to our invention can also be achieved using a motor that is driven using magnetic flux, and the type of motor or actuator used with our invention is therefore not specifically limited.

Furthermore, while a disc shaped ultrasonic motor is used in these embodiments as the ultrasonic motor, the invention shall obviously not be so limited. For example, the ultrasonic motor can use a rectangular, annular, or other shape of vibrator. In addition, the drive principle can use a standing wave or progressive wave. The shape or operating principle of the ultrasonic motor shall therefore not be specifically limited.

As described above, operating cost is low because it is only necessary to replace the tank unit when the solution runs out.

It is also possible to replace only the pump unit to, for example, change the type of solution, sterilize, or repair the pump unit.

It is yet further possible to adjust the dosage, dispensing rate, and other dispensing conditions while confirming the information on a display and also by replacing only the controller. It is therefore not necessary to change any parts of the solution delivery path when changing the dispensing conditions.

The time that dispensing is interrupted when changing the dispensing rate is therefore extremely short.

Furthermore, because the controller directly adjusts the dispensing conditions according to patient (biological) information, dosage can be easily optimally adjusted even if a person with specialized knowledge is not present.

The load on the pump unit is also low because the solution in the solution tank is pressurized by a pressure applying means and can thus flow easily from the solution tank.

Furthermore, the size of the pump unit is reduced and the portability of the portable dosing apparatus is improved if a compact ultrasonic motor or piezoelectric actuator with high output per unit volume is used as the drive source for the pump unit.

Furthermore, because the ultrasonic motor and piezoelectric actuator are not magnetically driven, there is substantially no chance of misoperation when close to a magnetic device. The reliability of the portable dosing apparatus is thus improved.

Furthermore, because the ultrasonic motor or piezoelectric actuator directly drive the pump unit, a power transfer mechanism is not needed, and a compact, lightweight pump unit can thus be achieved.

The number of parts is also reduced and manufacturing cost can therefore be kept down.

The reliability of the portable dosing apparatus is yet further improved as a result of the controller controlling the pump unit while monitoring pump unit operation, and a backflow prevention means significantly lowers the chances that the pump will operate in reverse or the solution backflow will occur.

Although the present invention has been described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart there from.

What is claimed is:

1. A portable solution delivery apparatus for supplying a body with a solution at a dispensing rate that can be varied, comprising:
   a tank unit for holding the solution;
   a pump unit for pumping the solution from the tank unit to the body;
   a controller for controlling the pump unit; and
   a housing in which the tank unit, the pumping unit, and the controller are removably disposed, the housing being removably mountable to the body.

2. A portable solution delivery apparatus according to claim 1; further comprising operation detection means for detecting pump unit operation and outputting a detection signal to the controller.

3. A portable solution delivery apparatus according to claim 1; wherein the controller comprises dispensing parameter input means for externally inputting a dispensing parameter; and a display for displaying a dispensing parameter; and wherein the controller controls the pump unit according to the input dispensing parameter.

4. A portable solution delivery apparatus according to claim 1; further comprising status information input means for inputting status information indicative of a condition of the body; wherein the controller controls the pump unit according to status information from the status information input means.

5. A portable solution delivery apparatus according to claim 1; wherein the tank unit comprises a solution tank that is expandable for internally storing the solution; and pressure applying means for applying pressure to the solution tank so as to reduce an internal volume of the solution tank so as to pressurize the solution.

6. A portable solution delivery apparatus according to claim 1; wherein the pump unit comprises an actuator driven according to a drive signal from the controller; a drive power transfer mechanism for transferring drive power from the actuator; and a pump for pumping solution by means of drive power transferred from the drive power transfer mechanism.

7. A portable solution delivery apparatus according to claim 6; wherein the actuator is an ultrasonic motor.

8. A portable solution delivery apparatus according to claim 6; wherein the actuator is a piezoelectric actuator.

9. A portable solution delivery apparatus according to claim 6; wherein the pump unit further comprises a ratchet mechanism connected to one of the drive power transfer mechanism and the pump for preventing backflow of the drive power.

10. A portable solution delivery apparatus according to claim 1; wherein the pump unit comprises an actuator driven according to a drive signal from the controller; and a pump for pumping solution by means of drive power transferred from the actuator.

11. A portable solution delivery apparatus according to claim 10; wherein the actuator is an ultrasonic motor.

12. A portable solution delivery apparatus according to claim 10; wherein the actuator is a piezoelectric actuator.

13. A portable solution delivery apparatus according to claim 10; wherein the pump unit further comprises a ratchet mechanism connected to the pump for preventing backflow of the drive power.

14. A portable solution delivery apparatus according to claim 1; further comprising backflow prevention means for preventing the pump unit from operating in reverse.

15. A portable solution delivery apparatus according to claim 1; further comprising a needle disposed in a flow path of the solution for injecting solution into the body.

16. A portable solution delivery apparatus for delivering a solution to a body, comprising: a tank for holding the solution; a storage compartment having a path therein through which the solution is pumped; a piezoelectric actuator disposed in the storage compartment for pumping the solution by changing the capacity of the storage compartment by undergoing expanding and contracting movement; and a controller for controlling the piezoelectric actuator.

17. A portable solution delivery apparatus according to claim 16; wherein the controller comprises dispensing parameter input means for externally inputting a dispensing parameter; and a display for displaying a dispensing parameter; and wherein the controller controls the piezoelectric actuator according to the input dispensing parameter.

18. A portable solution delivery apparatus according to claim 16; further comprising status information input means for inputting status information indicative of a condition of the body; wherein the controller controls the piezoelectric actuator according to the status information.

19. A portable solution deliver apparatus according to claim 16; further comprising a needle provided in the flow path for injecting the solution into the body.

20. A portable solution delivery apparatus for delivering a solution to a body, comprising: a housing removably mountable to the body; a tank disposed in the housing for holding the solution; a pump unit disposed in the housing for pumping the solution from the tank to the body; a controller removably disposed in the housing for controlling the pump unit to deliver the solution at a desired dispensing rate; and a delivery device for supplying the solution to a desired part of the body; wherein the controller is removable and replaceable by another controller to change the dispensing rate of the solution.

21. A portable solution delivery apparatus according to claim 20; wherein the controller comprises dispensing parameter input means for externally inputting a dispensing parameter; and a display for displaying a dispensing parameter; wherein the controller controls the pump unit according to the input dispensing parameter.

22. A portable solution delivery apparatus according to claim 20; further comprising status information input means for inputting status information indicative of a condition of the body; wherein the controller controls the pump unit according to status information from the status information input means.

23. A portable solution delivery apparatus according to claim 20; wherein the tank unit comprises a solution tank that is expandable for internally storing the solution; and pressure applying means for applying pressure to the solution tank to reduce an internal volume of the solution tank so as to pressurize the solution.

24. A portable solution delivery apparatus according to claim 20; wherein the pump unit comprises an actuator driven according to a drive signal from the controller; a drive power transfer mechanism for transferring drive power from the actuator; and a pump for pumping solution by means of drive power transferred from the drive power transfer mechanism.

25. A portable solution delivery apparatus according to claim 24; wherein the actuator is an ultrasonic motor.

26. A portable solution delivery apparatus according to claim 24; wherein the actuator is a piezoelectric actuator.

27. A portable solution delivery apparatus according to claim 20; further comprising operation detection means for detecting pump unit operation and outputting a detection signal to the controller.

28. A portable solution delivery apparatus according to claim 20; further comprising backflow prevention means for preventing the pump unit from operating in reverse.

29. A portable solution delivery apparatus according to claim 20; wherein the deliver device comprises a needle disposed in a flow path of the solution for injecting the solution into the body.

* * * * *